US006841722B1

(12) United States Patent
Lin et al.

(10) Patent No.: US 6,841,722 B1
(45) Date of Patent: Jan. 11, 2005

(54) **NUCLEIC ACID ENCODING THE *ARABIDOPSIS* SSE1 PROTEIN AND A METHOD OF USING IT TO MODIFY PLANT STORAGE RESERVES**

(75) Inventors: Yun Lin, Somerville, MA (US); Lin Sun, West Roxbury, MA (US); Long V. Nguyen, Vacaville, CA (US); Howard M. Goodman, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/545,072

(22) Filed: Apr. 7, 2000

Related U.S. Application Data
(60) Provisional application No. 60/128,651, filed on Apr. 8, 1999.

(51) Int. Cl.[7] .............................. A01H 5/00; A01H 5/10; C12H 15/29; C12H 15/82

(52) U.S. Cl. .................. 800/298; 424/93.2; 435/320.1; 435/419; 435/252.3; 536/23.6; 800/306

(58) Field of Search ................................. 800/298, 306, 800/320, 284, 281; 424/93.2; 536/23.6, 23.2; 435/320.1, 419, 252.3, 252.2

(56) References Cited

U.S. PATENT DOCUMENTS

| | | | |
|---|---|---|---|
| 5,650,554 A | 7/1997 | Moloney | |
| 5,925,805 A | 7/1999 | Ohlrogge et al. | |

OTHER PUBLICATIONS

Storozhenko, S. et al., "Identification of an *Arabidopsis thaliana* cDNA encoding a HSP70–related protein belonging to the HSP110/SSE1 subfamily." 1996, FEBS Letters, vol. 390, pp. 113–118.*
Gordon–Kamm, W. J. et al., "Transformation of Maize Cells and Regeneration of Fertile Transgenic Plants." 1990, The Plant Cell, vol. 2, pp. 603–618.*
Dietrich, P. S. et al., "Isolation and Characterization of a Small Heat Shock Protein Gene from Maize." 1991, Plant Physiol., vol. 96, pp. 1268–1276.*
Leborgne–Castel, N. et al., "Overexpression of BiP in Tobacco Alleviates Endoplasmic Reticulum Stress." 1999, The Plant Cell, vol. 11, pp. 459–469.*
Lee, Jeong H. and Schoffl, F. "An Hsp70 antisense gene affects the expression of HSP70/HSC70, the regulation of HSF, and the acquisition of thermotolerance in transgenic *Arabidopsis thaliana*." 1996, Mol. Gen. Genet., vol. 252, pp. 11–19.*
Arndt, G. M. and Rank, G. H. , Colocalization of antisense RNAs and ribozymes with their target mRNAs. 1997, Genome, vol. 40, pp. 785–797.*

Akama, K. et al., "Efficient transformation of *Arabidopsis thaliana*: comparison of the efficiencies with various organs, plant ecotypes and Agrobacterium strains." 1992, Plant Cell Reports, vol. 12, pp. 7–11.*
Tang, G., et al., "Antisense Repression of Vacuolar and Cell Wall Invertase in Transgenic Carrot Alters Early Plant Development and Sucrose Partitioning." 1999, The Plant Cell, vol. 11, pp. 177–189.*
Colliver, S. P. et al., "Differential modification of flavonoid and isoflavonoid biosynthesis with an antisense chalcone synthase construct in transgenic Lotus corniculatus." 1997, Plant Molecular Biology, vol. 35, pp. 509–522.*
Klann, E. M. et al., "Antisense Acid Invertase (TIV1) Gene Alters Soluble Sugar Composition and Size in Transgenic Tomato Fruit." 1996, Plant Physiol., vol. 112, pp. 1321–1330.*
Kuipers, A. G. J. et al., "Factors affecting the inhibition by antisense RNA of granule–bound starch synthase gene expression in potato." 1995, Mol. Gen. Genet, vol. 246, pp. 745–755.*
Bird, C. R. et al., "Using Antisense RNA to Study Gene Function: Inhibition of Carotenoid Biosynthesis in Transgenic Tomatoes." 1991, BIO/Technology, vol. 9, pp. 635–639.*
van der Krol, A. R. et al., "Inhibition of flower pigmentation by antisense CHS genes: promoter and minimal sequence requirements for the antisense effect." 1990, Plant Molecular Biology, vol. 14, pp. 457–466.*
Broun, P. et al., "Catalytic Plasticity of Fatty Acid Modification Enzymes Underlying Chemical Diversity of Plant Lipids." 1998, Science, vol. 282, pp. 1315–1317.*
Rounsley, S. D. et al., Accession Nos. T00882 and F84893, Feb. 12, 1999.*
Bowie, J. U. et al., "Deciphering the Message in Protein Sequences: Tolerance to Amino Acid Substitutions." 1990, Science, vol. 247, pp. 1306–1310.*
Hill, M. A. and Preiss, J. "Functional Analysis of Conserved Histidines in ADP–Glucose Pyrophosphorylase from *Escherichia coli*." 1998, Biochemical and Biophysical Res. Comm., vol. 244, pp. 573–577.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*
Mukai, H. et al., "Isolation and characterization of SSE1 and SSE2, new members of the yeast HSP70 multigene family." 1993, Gene, vol. 132, pp. 57–66.*
Galili, G. et al., "The endoplasmic reticulum of plant cells and its role in protein maturation and biogenesi of oil bodies." 1998, Plant Molecular Biology, vol. 38, pp. 1–29.*

(List continued on next page.)

*Primary Examiner*—Anne Kubelik
(74) *Attorney, Agent, or Firm*—Clark & Elbing LLP

(57) ABSTRACT

Disclosed is a *Arabidopsis* sse1 gene, which is responsible for protein and oil body biogenesis. The invention further provides methods for using the disclosed gene for modifying the components of plant storage reserve materials.

33 Claims, 8 Drawing Sheets

OTHER PUBLICATIONS

Bhave et al., "Identification and Molecular Characterization of Shrunken–2 cDNA Clones of Maize," *The Plant Cell* 2:581–588 (1990).

Lee et al., "Maize oleosin is correctly targeted to seed oil bodies in *Brassica napus* transformed with the maize oleosin gene," *Proc. Natl. Acad. Sci.* USA 88:6181–6185 (1991).

Chen et al., "Development of Protein Bodies and Accumulation of Carbohydrates in a Soybean (Leguminosae) Shriveled Seed Mutant," *Am. J. Bot.* 85:492–499,1998.

Chrispeels et al., "Sorting of Proteins in the Secretory System," *Annu. Rev. Plant Physiol. Plant Mol. Biol.* 42:21–53, 1991.

Eitzen et al., "Enlarged Peroxisomes Are Present in Oleic Acid–grown *Yarrowis lipolytica* Overexpressing the PEX16 Gene Encoding an Intraperoxisomal Peripheral Membrane Peroxin," *Journal of Cell Biology* 137:1265–1278, 1997.

Huang, "Oleosins and Oil Bodies in Seeds and Other Organs," *Plant Physiol.* 110:1055–1061, 1996.

Lin et al., "The Pex 16p Homolog SSE1 and Storage Organelle Formation in Arabidopsis Seeds," *Science* 284:328–330, 1999.

Liu et al., "Efficient Isolation and mapping of *Arabidopsis thaliana* T–DNA insert junctions by thermal asymmetric interlaced PCR," *Plant Journal* 8:457–463, 1995.

Meinke et al., "Leafy Cotyledon Mutants of Arabidopsis," *Plant Cell* 6:1049–1064, 1994.

Olsen et al., "Peroxisomes and Their Assembly in Higher Plants," *Annu. Rev. Plant Physiol. Plant Mol. Biol.* 46:123–146, 1995.

Sarmiento et al., "Expression and subcellular targeting of a soybean oleosin in transgenic rapeseed. Implications for the mechanism of oil–body formation in seeds," *Plant Journal* 11:783–796, 1997.

Titorenko et al., "Four Distinct Secretory Pathways Serve Protein Secretion, Cell Surface Growth, and Peroxisome biogenesis in the Yeast *Yarrowia lipolytica*," *Molecular and Cellular Biology* 17:5210–5226, 1997.

Titorenko et al., "Mutants on the Yeast *Yarrowi Lipolytica* Defective in Protein Exit from the Endoplasmic Reticulum Are Also Defective in Peroxisome Biogenesis," *Molecular and Cellular Biology* 18:2789–2803, 1998.

* cited by examiner

```
   1 attgcaacca ggaagagaaa gaaaatcaga gattgattta acgtgaatgg aattttgttg
  61 tttcccaaat tcttctgaga aatagcaaag ttcagttttg tttctctcta tctgaagctc
 121 aatggaagct tataagcaat gggtttggag aaatagagag tatgtacaat cctttggatc
 181 ctttgccaac ggattgacat ggctgcttcc tgagaagttt tctgcttcag agattggacc
 241 agaagcagta acggctttt tgggcatatt cacaacgata aatgaacaca taattgaaaa
 301 tgctccaaca cctcgtggcc atgttggatc ttccgggaat gatccatccc tttcttatcc
 361 actactcatc gccatcctca aggatttgga aactgttgtg gaagtggcag ctgaacactt
 421 ctatggagac aaaaaatgga actacattat tctcactgaa gctatgaagg ctgtcattag
 481 gttagccttg ttccggaata gtgggtataa gatgcttctt caaggagggg aaacacctaa
 541 tgaggagaaa gattctaacc aatccgagtc gcaaaataga gctggtaatt cgggtagaaa
 601 tctcgggcct catggtcttg gaaaccaaaa tcatcataat ccatggaact tggaaggacg
 661 ggcgatgtct gctttaagtt catttggtca gaatgcaaga acaacaacat cttctacccc
 721 cggttggtct cgaagaattc aacatcagca agcagttata gagcctccaa tgatcaagga
 781 gaggcgaaga acgatgtccg agctacttac tgagaagggt gttaatggag cgttgtttgc
 841 gattggtgag gttctttaca taacgagacc gctcatttac gttcttttca tcagaaaata
 901 tggagtccga tcttggattc cttgggctat atcgctttct gtggacacac tggggatggg
 961 tcttcttgca aattcgaagt ggtggggaga gaagagcaag caagtccatt tctcaggacc
1021 tgaaaaggat gagctgagga gacgaaaact gatatgggca ttgtacctca tgagagatcc
1081 attcttcacc aagtacacaa ggcagaagct ggaaagctct caaaagaagc tggaactaat
1141 tccattgatc ggattcctca cagagaagat tgtggagctt tggagggag ctcagtcacg
1201 gtacacttac atatcgggat cgtgaggtta agcgttttac ttatggttta tatgcaacgg
1261 aagaatattg ccattgttgg aatgctttt tagatcatca aaggctccta cagatttctt
1321 agggaatggt ttcaggcttt tgttagaaat tgtgtttatt gcaacaggta gagaacataa
1381 ccatagacag atgtatctga agagataagc ttctctatgt ctaaagaaat ggaccgatac
1441 gaataaaaca agcatcatta aagattaaaa aaaaaaaaaa aaa
```

Fig. 2A

```
MEAYKQWVWR NREYVQSFGS FANGLTWLLP EKFSASEIGP EAVTAFLGIF TTINEHIIEN
APTPRGHVGS SGNDPSLSYP LLIAILKDLE TVVEVAAEHF YGDKKWNYII LTEAMKAVIR
LALFRNSGYK MLLQGGETPN EEKDSNQSES QNRAGNSGRN LGPHGLGNQN HHNPWNLEGR
AMSALSSFGQ NARTTTSSTP GWSRRIQHQQ AVIEPPMIKE RRRTMSELLT EKGVNGALFA
IGEVLYITRP LIYVLFIRKY GVRSWIPWAI SLSVDTLGMG LLANSKWWGE KSKQVHFSGP
EKDELRRRKL IWALYLMRDP FFTKYTRQKL ESSQKKLELI PLIGFLTEKI VELLEGAQSR
YTYISGS
```

Fig. 2B

```
SSE1           MEAVKQWVWRNREYVQSFGSFANGLTWLLPE  31
Pex16p  MTDKLVKVMQKKKSAPQTWLDSYDKFLVRNAASIGSIESTLRTVSYVLPG  50

SSE1    KFSASEIGPEAVTAFLGIFTTINEHIIENA............PTPRGHVG  69
Pex16p  RFNDVEIATETLYAVLNVLGLYHDTIIARAVAASPNAAAVYRPSPHNRYT 100

SSE1    S..SGNDPSLSY.PLLIAILKDLETVVEVAAEHFYGD.KKWNYIILTEAM 115
Pex16p  DWFIKNRKGYKYASRAVTFVKFGELVAEMVAKKNGGEMARWKCIIGIEGI 150

*
SSE1    KAVIRLALFRNSGYKMLLQGGETPNEEKDSNQSESQNRAGNSGRNLGPHG 165
Pex16p  KAGLRIYMLGSTLYQPLC...TTPYPDREVTGELLETICRDEGELDIEKG 197

SSE1    LGNQNHHNPWNLEGRAMSALSSFGQNARTTTSSTPGWSRRIQHQQAVIEP 215
Pex16p  LMDPQWKMP..RTGRTIPEIAPTNVEGYLLT........KVLRSEDVDRP 237

SSE1    PMIKERRRTMSELLTEKGVNGALFAIGEVLYITRPLIYVLFIRKYGVRS. 264
Pex16p  YNLLSR.......LDNWGV......VAELLSILRPLIYACLLFRQHVNKT 274

SSE1    ..............WIPWAISLSVDTLGMGLLANSKWWGEKSKQVHFSG 299
Pex16p  VPASTKSKFPFLNSPWAPWIIGLVIEALSRKMMGS...WLLRQRQSGKTP 321

SSE1    PEKD..ELRRRKLIWALYLMRDPFFTKYTRQKLESSQKKLELIPLIGFLT 347
Pex16p  TALDQMEVKGRTNLLGWWLFRGEFYQAYTRPLLYSIVARLEKIPGLGLFG 371

SSE1    EKIVELLEGAQSRYTYISGS   367
Pex16p  ALISDYLY.LFDRYYFTASTL  391
```

Fig. 4A

NUCLEIC ACID ENCODING THE *ARABIDOPSIS* SSE1 PROTEIN AND A METHOD OF USING IT TO MODIFY PLANT STORAGE RESERVES

BACKGROUND OF THE INVENTION

This application claims benefit of U.S. provisional application 60/128,651, filed on Apr. 8, 1999.

This invention relates to the deposition of plant storage reserve materials (e.g., seed reserve material), the biogenesis of storage organelles, and the production of transgenic plants having altered storage reserve profiles.

Flowering plants deposit extra food reserves in their seeds to support young seedling growth. The storage compounds in various seeds are principally composed of carbohydrates, proteins, and lipids. The relative amounts of these substances, however, differ widely among species (Bewley and Black, *Seeds: Physiology of Development and Germination*, Plenum Press, New York, $2^{nd}$ edition, Chap 1, 1994). For instance, cereal plants deposit relatively more carbohydrates, while legume seeds and oilseeds contain relatively more proteins and lipids, respectively (Bewley and Black, supra; Vitale and Bollini, In: *Seed Development and Germination*, J. Kigel and G. Galili, eds., Marcel Dekker, Inc., New York, 1995, pp. 73–102; Miquel and Browse, ibid, pp. 169–193). Although these variations are largely controlled by genetic factors, the molecular mechanisms that account for these different developmental programs for storage deposition are mostly unknown.

Directly and indirectly (through feeding to livestock), seeds also make up the major sources of human diet. Therefore, improving the nutritive value of crop seeds has been of great interest. The efforts to date, however, have been made mainly through breeding (Payne, In: *Seed Proteins*, J. Daussant, J. Mosse, and J. Vaughan, eds. Academic Press, London, 1983, pp. 223–253; W. Gottschalk and H. P. Muller, eds, *Seed Proteins: Biochemistry*, Genetics, Nutritive Value, The Hague, The Netherlands, 1983).

SUMMARY OF THE INVENTION

In general, the invention features an isolated nucleic acid molecule which includes a sequence encoding an SSE polypeptide. Preferably, the isolated nucleic acid molecule which includes a sequence encoding a polypeptide that is substantially identical to SSE1 (SEQ ID NO:2). In other preferred embodiments, the sequence encodes an SSE polypeptide having at least 30% identity with the amino acid sequence shown in FIG. 2B (SEQ ID NO:2). In other preferred embodiments, the sequence encodes an SSE polypeptide that, when expressed in a cell of a plant, modifies or alters the production of a food storage reserve material (e.g., protein, lipid, or carbohydrate storage reserve); facilitates the intracellular transport of a storage protein; or facilitates the formation of protein or oil bodies. In still other preferred embodiments, the nucleic acid molecule is a cDNA molecule.

In another aspect, the invention features an isolated nucleic acid molecule which includes a sequence that encodes an SSE polypeptide, wherein the isolated nucleic acid molecule hybridizes specifically to a nucleic acid molecule that includes the cDNA of FIG. 2A (SEQ ID NO:1). In preferred embodiments, the isolated nucleic acid sequence encodes an SSE polypeptide having at least 30% identity with the amino acid sequence shown in FIG. 2B (SEQ ID NO:2).

In related aspects, the invention features a transgenic plant (or plant cell, plant tissue, plant organ, or plant component) which includes a recombinant transgene that expresses an SSE polypeptide, wherein the transgene is expressed in the transgenic plant under the control of an expression control region that is functional in a plant cell. The invention further features seeds and cells produced by a transgenic plant which includes such a recombinant transgene.

In other related aspects, the invention features a sense-oriented expression vector which includes any of the aforementioned nucleic acid molecules; the vector being capable of directing expression of the SSE polypeptide encoded by the nucleic acid molecule. In this regard, the invention also includes a cell (e.g., a bacterial or plant cell) or a transgenic plant or transgenic plant component that includes such an expression vector.

In other aspects, the invention features an expression vector for producing antisense SSE RNA; a transgenic plant or transgenic plant component including such an antisense vector; and seeds or cells produced by a transgenic plant or transgenic plant component that express the antisense construct.

In another aspect, the invention features a substantially pure SSE polypeptide that includes an amino acid sequence having at least 30% identity to the amino acid sequence of FIG. 2B (SEQ ID NO:2). In preferred embodiments, the polypeptide modifies or alters the production of a storage reserve (e.g., a protein or lipid storage reserve); facilitates the intracellular transport of a storage protein or lipid; or facilitates the formation of protein bodies or oil bodies.

In another aspect, the invention features a method of producing an SSE polypeptide, the method includes the steps of: (a) providing a cell transformed with a nucleic acid molecule of the invention positioned for expression in the cell; (b) culturing the transformed cell under conditions for expressing the nucleic acid molecule; and (c) recovering the SSE polypeptide. Recombinant SSE polypeptides produced using this method are also included in the invention.

In another aspect, the invention features a substantially pure antibody that specifically recognizes and binds to an SSE polypeptide or a portion thereof. In preferred embodiments, the antibody specifically recognizes and binds to a recombinant SSE polypeptide or a portion thereof.

In another aspect, the invention features a method of isolating an SSE gene or fragment thereof, the method including the steps of: (a) contacting the nucleic acid molecule of FIG. 2A (SEQ ID NO:1) or a portion thereof with a nucleic acid preparation from a plant cell under hybridization conditions providing detection of nucleic acid sequences having at least 30% or greater sequence identity to the nucleic acid sequence of FIG. 2A (SEQ ID NO:1); and (b) isolating the hybridizing nucleic acid sequences.

In still another aspect, the invention features a method of isolating an SSE gene or fragment thereof, the method including the steps of: (a) providing a sample of plant cell DNA; (b) providing a pair of oligonucleotides having sequence identity to a region of the nucleic acid of FIG. 2A (SEQ ID NO:1); (c) contacting the pair of oligonucleotides with the plant cell DNA under conditions suitable for polymerase chain reaction-mediated DNA amplification; and (d) isolating the amplified SSE gene or fragment thereof. In preferred embodiments, the amplification step is carried out using a sample of cDNA prepared from a plant cell. In still other preferred embodiments, the pair of oligonucleotides used in the amplification step are based on a sequence encoding an SSE polypeptide, wherein the SSE polypeptide is at least 30% identical to the amino acid sequence of FIG. 2B (SEQ ID NO:2).

In another aspect, the invention features a method for modifying or altering the biosynthesis of a storage reserve in a transgenic plant or transgenic plant component, the method including the steps of: (a) introducing into a plant cell a transgene including DNA encoding an SSE polypeptide having at least 20% identity to the SSE1 polypeptide (SEQ ID NO:2) operably linked to a promoter functional in plant cells to yield a transformed plant cells; and (b) regenerating a transgenic plant or transgenic plant component from said transformed cells, wherein the SSE polypeptide is expressed in the cells of said transgenic plant or transgenic plant component, thereby modifying or altering the seed storage reserve of said transgenic plant or transgenic plant component. In preferred embodiments, the storage reserve material is a lipid, a storage protein, or a carbohydrate (e.g., a starch). In preferred embodiments, the expressed polypeptide is Pex16 (SEQ ID NO:6). In other preferred embodiments, the storage reserve is a seed or vegetative storage reserve material.

In another aspect, the invention features a method for modifying or altering the biosynthesis of a storage reserve in a transgenic plant cell, the method including reducing the level of an SSE polypeptide (or expression of an SSE gene) in a transgenic plant or transgenic plant component. In preferred embodiments, the method for reducing the level of the SSE polypeptide includes expressing an antisense SSE nucleic acid sequence in the transgenic plant or transgenic plant component. In other preferred embodiments, the method for reducing the level of an SSE polypeptide includes co-suppression of an SSE nucleic acid sequence in the transgenic plant or transgenic plant component. Preferably, the storage reserve material is a lipid, a storage protein, or a carbohydrate (e.g., a starch). In yet other preferred embodiments, the storage reserve is a seed or vegetative storage reserve material.

In yet another aspect, the invention features a process for modifying storage protein production in a transgenic plant or transgenic plant component, the method including the steps of: (a) introducing into plant cells a transgene encoding an SSE polypeptide operably linked to a promoter functional in the plant cells to yield transformed plant cells; and (b) regenerating a transgenic plant or transgenic plant component from the transformed plant cells, wherein the SSE polypeptide is expressed in the cells of the transgenic plant or transgenic plant component, thereby modifying storage protein production in the transgenic plant or transgenic plant component. In preferred embodiments, the transgene encoding the SSE polypeptide is overexpressed. In other preferred embodiments, the transgene encoding the SSE polypeptide is constitutively expressed, is inducibly expressed, or is expressed in a tissue-specific, cell-specific, or organ-specific manner. Preferably, storage protein production is increased relative to an untransformed control plant or plant component.

In a related aspect, the invention also features a process for modifying storage protein production in a transgenic plant or transgenic plant component, the method including the steps of: (a) introducing into plant cells a transgene encoding an antisense coding sequence of an SSE polypeptide operably linked to a promoter functional in the plant cells to yield transformed plant cells; and (b) regenerating a transgenic plant or transgenic plant component from the transformed plant cells, wherein the antisense coding sequence of the SSE polypeptide is expressed in the cells of the transgenic plant or transgenic plant component, thereby modifying storage protein production in the transgenic plant or transgenic plant component. In preferred embodiments, the transgene encoding an antisense coding sequence of an SSE polypeptide is overexpressed. In other preferred embodiments, the transgene encoding an antisense coding sequence of an SSE polypeptide is constitutively expressed. Preferably, the transgene encodes an antisense coding sequence of an SSE polypeptide is inducibly expressed or is expressed in a tissue-specific, cell-specific, or organ-specific manner. Preferably, storage protein production is decreased relative to an untransformed control plant or plant component.

In another aspect, the invention features a process for modifying storage lipid production in a transgenic plant or transgenic plant component, the method including the steps of: (a) introducing into plant cells a transgene encoding an SSE polypeptide operably linked to a promoter functional in the plant cells to yield transformed plant cells; and (b) regenerating a transgenic plant or transgenic plant component from the transformed plant cells, wherein the SSE polypeptide is expressed in the cells of the transgenic plant or transgenic plant component, thereby modifying storage lipid production in the transgenic plant or transgenic plant component. In preferred embodiments, the transgene encoding the SSE polypeptide is overexpressed. In other preferred embodiments, the transgene encoding the SSE polypeptide is constitutively expressed, is inducibly expressed, or is expressed in a tissue-specific, cell-specific, or organ-specific manner. Preferably, storage lipid production is increased relative to an untransformed control plant or plant component.

In another aspect, the invention features a process for modifying storage lipid production in a transgenic plant or transgenic plant component, the method including the steps of: (a) introducing into plant cells a transgene encoding an antisense coding sequence of an SSE polypeptide operably linked to a promoter functional in the plant cells to yield transformed plant cells; and (b) regenerating a transgenic plant or transgenic plant component from the transformed plant cells, wherein the antisense coding sequence of the SSE polypeptide is expressed in the cells of the transgenic plant or transgenic plant component, thereby modifying storage lipid production in the transgenic plant or transgenic plant component. In preferred embodiments, the transgene encoding an antisense coding sequence of an SSE polypeptide is overexpressed. In other preferred embodiments, the transgene encoding an antisense coding sequence of an SSE polypeptide is constitutively expressed. Preferably, the transgene encodes an antisense coding sequence of an SSE polypeptide is inducibly expressed or is expressed in a tissue-specific, cell-specific, or organ-specific manner. Preferably, storage lipid production is decreased relative to an untransformed control plant or plant component.

In another aspect, the invention features a process for modifying storage carbohydrate production in a transgenic plant or transgenic plant component, the method including the steps of: (a) introducing into plant cells a transgene encoding an SSE polypeptide operably linked to a promoter functional in the plant cells to yield transformed plant cells; and (b) regenerating a transgenic plant or transgenic plant component from the transformed plant cells, wherein the SSE polypeptide is expressed in the cells of the transgenic plant or transgenic plant component, thereby modifying storage carbohydrate production in the transgenic plant or transgenic plant component. In preferred embodiments, the transgene encoding the SSE polypeptide is overexpressed. In other preferred embodiments, the transgene encoding the SSE polypeptide is constitutively expressed, is inducibly expressed, or is expressed in a tissue-specific, cell-specific, or organ-specific manner. Preferably, storage carbohydrate production (e.g., starch production) is decreased relative to an untransformed control plant or plant component.

In another aspect, the invention features a process for modifying storage carbohydrate production in a transgenic plant or transgenic plant component, the method including the steps of: (a) introducing into plant cells a transgene encoding an antisense coding sequence of an SSE polypeptide operably linked to a promoter functional in the plant cells to yield transformed plant cells; and (b) regenerating a transgenic plant or transgenic plant component from the transformed plant cells, wherein the antisense coding sequence of the SSE polypeptide is expressed in the cells of the transgenic plant or transgenic plant component, thereby modifying storage carbohydrate production in the transgenic plant or transgenic plant component. In other preferred embodiments, the transgene encoding an antisense coding sequence of an SSE polypeptide is constitutively expressed. Preferably, the transgene encodes an antisense coding sequence of an SSE polypeptide is inducibly expressed or is expressed in a tissue-specific, cell-specific, or organ-specific manner. Preferably, storage carbohydrate production (e.g., starch production) is increased relative to an untransformed control plant or plant component.

In another aspect, the invention features a process for modifying dessication tolerance of a transgenic plant or transgenic plant component, the method including the steps of: (a) introducing into plant cells a transgene encoding an antisense coding sequence of an SSE polypeptide operably linked to a promoter functional in the plant cells to yield transformed plant cells; and (b) regenerating a transgenic plant or transgenic plant component from the transformed plant cells, wherein the antisense coding sequence of the SSE polypeptide is expressed in the cells of the transgenic plant or transgenic plant component, thereby modifying dessication tolerance of the transgenic plant or transgenic plant component. In preferred embodiments, the dessication tolerance of the transgenic plant or transgenic plant component is increased relative to an untransformed control plant or plant component.

By "shrunken seed" gene or "SSE" gene is meant a gene encoding a polypeptide that governs or regulates protein and oil body biogenesis in a plant cell. SSE genes may be identified and isolated from any plant species, especially agronomically important crop plants, using any of the sequences disclosed herein in combination with conventional methods known in the art.

By "polypeptide" is meant any chain of amino acids, regardless of length or post-translational modification (for example, glycosylation or phosphorylation).

By "substantially identical" is meant a polypeptide or nucleic acid exhibiting at least 30%, preferably 50%, more preferably 80%, and most preferably 90%, or even 95% homology to a reference amino acid sequence (for example, the amino acid sequence shown in FIG. 2B (SEQ ID NO:2) or nucleic acid sequence (for example, the nucleic acid sequences shown in FIG. 2A (SEQ ID NO:1)). For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, or PILEUP/PRETTYBOX programs). For example, such software when set to standard parameters matches identical or similar sequences by assigning degrees of homology to various substitutions, deletions, and/or other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant an SSE polypeptide (for example, an SSE polypeptide such as SSE1 (SEQ ID NO:2)) that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, an SSE polypeptide. A substantially pure SSE polypeptide may be obtained, for example, by extraction from a natural source (for example, a plant cell); by expression of a recombinant nucleic acid encoding an SSE polypeptide; or by chemically synthesizing the protein. Purity can be measured by any appropriate method, for example, column chromatography, polyacrylamide gel electrophoresis, or by HPLC analysis.

By "derived from" or "obtained from" is meant isolated from or having the sequence of a naturally-occurring sequence (e.g., a cDNA, genomic DNA, synthetic, or a combination thereof).

By "isolated nucleic acid molecule" is meant a DNA molecule that is free of the genes which, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA which is part of a hybrid gene encoding additional polypeptide sequence.

By "hybridizes specifically" is meant that a nucleic acid sequence hybridizes to a DNA sequence at least under low stringency conditions as described herein, and preferably under high stringency conditions, also as described herein.

By "antisense SSE" is meant a nucleotide sequence that is complementary to an SSE (or SSE homolog) messenger RNA. In general, such an antisense sequence will usually be at least 15 nucleotides, preferably about 15–200 nucleotides, and more preferably 200–2,000 nucleotides in length. The antisense sequence may be complementary to all or a portion of the SSE or SSE homolog mRNA nucleotide sequence (for example, the SSE1 gene), and, as appreciated by those skilled in the art, the particular site or sites to which the antisense sequence binds as well as the length of the antisense sequence will vary, depending upon the degree of inhibition desired and the uniqueness of the antisense sequence. A transcriptional construct expressing an SSE antisense nucleotide sequence includes, in the direction of transcription, a promoter, the sequence coding for the antisense RNA on the sense strand, and a transcriptional termination region. Antisense SSE sequences may be constructed and expressed according to standard methods, for example, in van der Krol et al., Gene 72:45, 1988; Rodermel et al., Cell 55:673, 1988; Mol et al., FEBS Lett. 268:427, 1990; Weigel and Nilsson, Nature 377:495, 1995; Cheung et al., Cell 82:383, 1995; and U.S. Pat. No. 5,107,065.

By "transformed cell" is meant a cell into which (or into an ancestor of which) has been introduced, by means of recombinant DNA techniques, a DNA molecule encoding (as used herein) an SSE polypeptide.

By "positioned for expression" is meant that the DNA molecule is positioned adjacent to a DNA sequence which directs transcription and translation of the sequence (i.e., facilitates the production of, for example, an SSE polypeptide, a recombinant protein, or an RNA molecule).

By "reporter gene" is meant a gene whose expression may be assayed; such genes include, without limitation, β-glucuronidase (GUS), luciferase, chloramphenicol transacetylase (CAT), green fluorescent protein (GFP), β-galactosidase, herbicide resistant genes and antibiotic resistance genes.

By "expression control region" is meant any minimal sequence sufficient to direct transcription. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements or chemical inducers); such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, *cyanobacteria*, seeds, suspension cultures, embryos, meristematic regions, callus tissue, leaves, roots, shoots, gametophytes, sporophytes, pollen, and microspores.

By "crucifer" is meant any plant that is classified within the Cruciferae family. The Cruciferae include many agricultural crops, including, without limitation, rape (for example, *Brassica campestris* and *Brassica napus*), broccoli, cabbage, brussel sprouts, radish, kale, Chinese kale, kohlrabi, cauliflower, turnip, rutabaga, mustard, horseradish, and *Arabidopsis*.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome. A transgenic plant according to the invention may contain one or more acquired resistance genes.

By "detectably-labelled" is meant any direct or indirect means for marking and identifying the presence of a molecule, for example, an oligonucleotide probe or primer, a gene or fragment thereof, or a cDNA molecule or a fragment thereof. Methods for detectably-labelling a molecule are well known in the art and include, without limitation, radioactive labelling (for example, with an isotope such as $^{32}P$ or $^{35}S$) and nonradioactive labelling (for example, chemiluminescent labelling, for example, fluorescein labelling).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, for example, an acquired resistance polypeptide-specific antibody. A purified SSE antibody may be obtained, for example, by affinity chromatography using a recombinantly-produced acquired resistance polypeptide and standard techniques.

By "specifically binds" is meant an antibody which recognizes and binds an SSE protein but which does not substantially recognize and bind other molecules in a sample, for example, a biological sample, which naturally includes an SSE protein such as SSE1.

As discussed above, a fundamental gene that is responsible for protein and oil body biogenesis has been identified. Accordingly, the invention provides a number of important advances and advantages for engineering plant storage reserves, including seed and vegetative reserve storage material. For example, by providing SSE genes as described herein that are readily incorporated and expressed in all species of plants, the invention facilitates an effective and economical means for producing plants having increased nutritional value. In addition, because plants expressing an SSE gene are dessication tolerant, the invention further provides for increased production efficiency, as well as for improvements in quality and yield of crop plants and ornamentals. Thus, the invention contributes to the production of high quality and high yield agricultural products: for example, fruits, ornamentals, vegetables, legumes, cereals and field crops.

The invention is also useful for providing nucleic acid and amino acid sequences of an SSE gene that facilitates the isolation and identification of SSE genes from any plant species.

Other features and advantages of the invention will be apparent from the following description of the preferred embodiments thereof, and from the claims.

DETAILED DESCRIPTION

The drawings will first be described.

DRAWINGS

FIG. 1 is a panel of photographs showing the abnormal storage deposition and the shrunken phenotype of sse1 seeds. FIGS. 1A and 1B are transmission electron micrographs of a representative cell from the wild-type cotyledon and hypocotyl, respectively. FIGS. 1C and 1D are transmission electron micrographs of a representative cell from the sse1 cotyledon and hypocotyl, respectively. Wild-type cells are filled with numerous oil bodies (OB) and a few large protein bodies (PB). sse1 cells contained few oil bodies and additional structures such as starch granules (St), vacuoles (Vc), stacks of membranes (M), and vesicles (Vs). FIGS. 1E and 1F show photographs of wild-type C24 and sse1 seeds, respectively. The magnification bar found in FIGS. 1A–1D is 3.1 μM. For histological examination, mature wild-type C24 and once backcrossed sse1 seeds were used. sse1 seeds were imbibed in water for 20 minutes before processing. Seeds were cut into halves and fixed in 2.5% glutaraldehyde/ 0.1 M cacodylate buffer (pH 7.2), post-fixed in 1% osmium tetroxide, dehydrated in an ethanol series, and embedded in Spurr's resin. Thin sections were then stained with uranyl acetate and observed under a transmission electron microscope.

FIG. 2A shows the cDNA sequence (SEQ ID NO:1) of SSE1. The ATG start codon and TGA stop codon of the SSE1 gene are located at positions 122 and 1223, respectively.

FIG. 2B shows the predicted amino acid sequence of SSE1 (SEQ ID NO:2) encoded by the cDNA shown in FIG. 2A. Hydrophobic (single line) and hydrophilic (double line) regions of the polypeptide are underlined.

FIG. 4A shows the amino acid sequence alignment of SSE1 (SEQ ID NO:2) and Pex16p (SEQ ID NO:6). Dots indicate gaps. Identical residues are boxed. Hydrophobic (single line) and hydrophilic (double line) regions for both proteins are underlined (Kyte and Doolittle, J. Mol. Biol. 157:105, 1982). The predicted glycosylation site of SSE1 is indicated with an asterisk. Single-letter abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

Figure 4B:

FIG. 4B shows the phenotype of seeds obtained from sse1 plants expressing the SSE1 transgene.

Figure 4C:
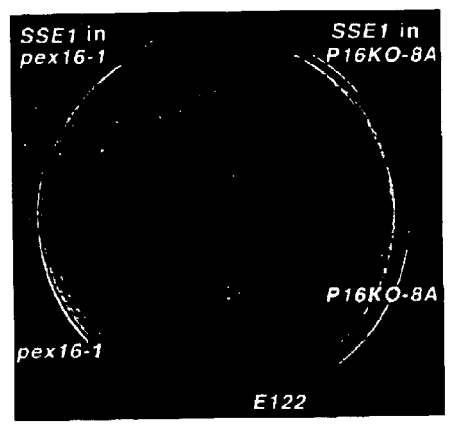

FIG. 4C shows the SSE1 complementation of pex16 mutants pex16-1 and P16KO-8A (Eitzen et al., J. Cell Biol. 137:1265, 1997) for growth on oleic acid as sole carbon source. SSE1 cDNA was cloned into the EcoRI site of a *Y. lipolytica* shuttle vector pTc3 between the promoter and the terminator regions of *Y. lipolytica* thiolase gene. Ura+ transformants of pex16-1 and P16KO-8A were obtained as described by Eitzen et al. (supra). E122 is the wild-type strain.

Figure 4D:

FIG. 4D shows SSE1 complementation of pex16-1 mutant for the dimorphic transition from yeast to mycelia form. Cells were grown at 30° C. in YND liquid medium (Eitzen et al., supra). The SSE1 transformant underwent dimorphic transition at a lower frequency than the wild-type strain E122.

Figure 5:
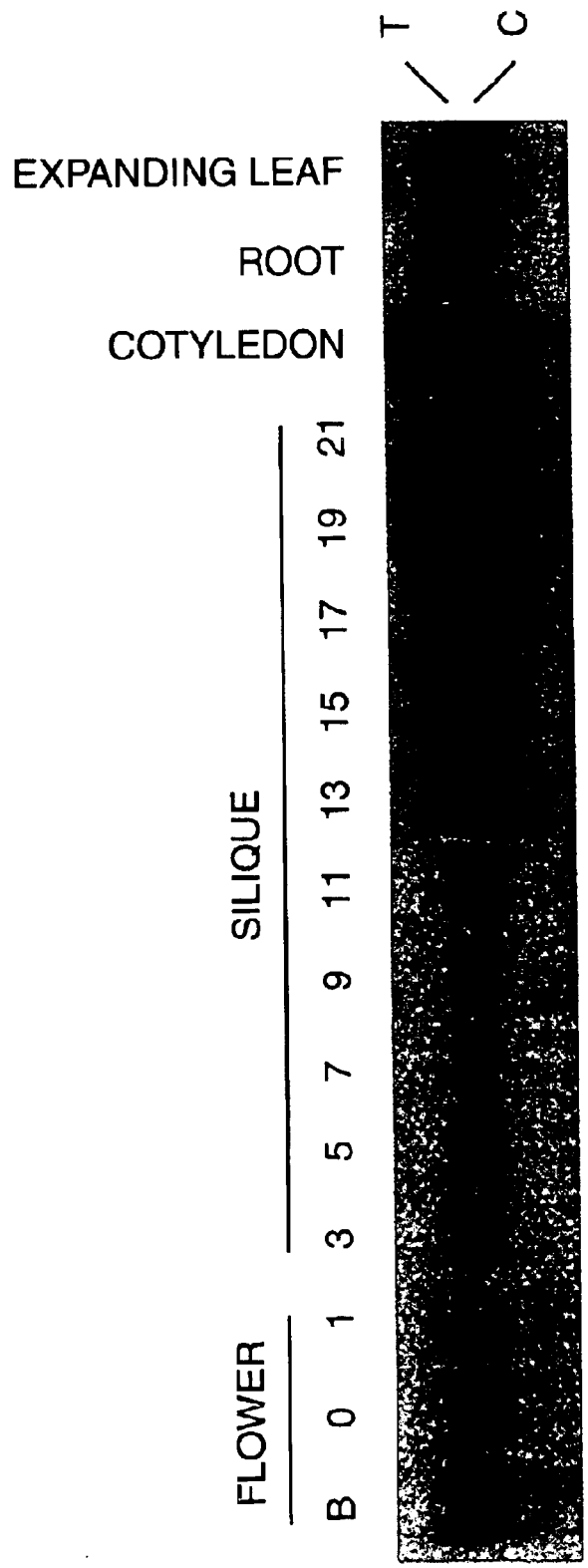

FIG. 5 shows the results of competitive RT-PCR analyses of SSE1 expression profiles. RNA was isolated from flowers before (B), on the day (0), or 1 day after pollination (1); from siliques 3 to 21 days after pollination; from cotyledons of 2-day-old seedlings; and from expanding rosette leaves and roots. An equal amount of competitor cDNA template was included in each reaction. The SSE1 target (T)-to-competitor (C) cDNA ratios reflect the relative expression levels of the SSE1 gene.

Abnormal Storage Deposition and the Shrunken Phenotype of sse1 Seeds

Figure 1A:
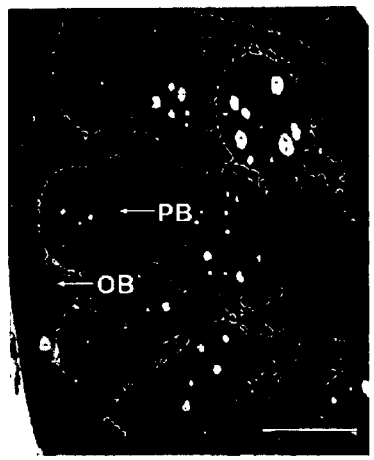
Figure 1B:
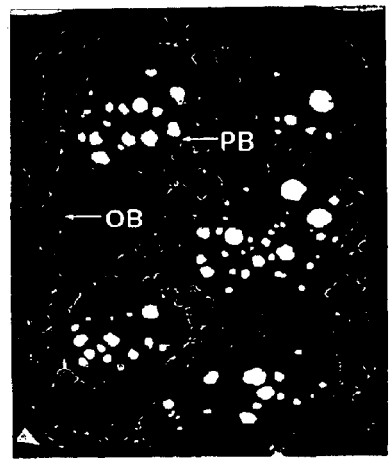
Figure 1C:
Figure 1D:
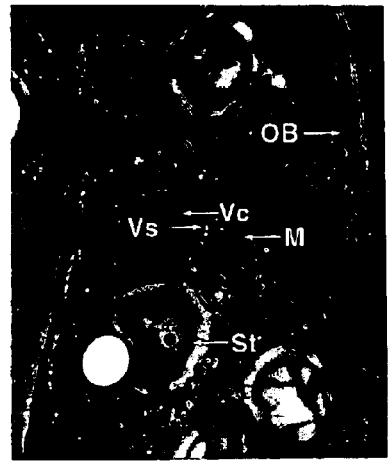
Figure 1E:
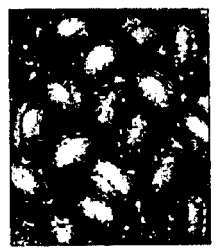
Figure 1F:

In *Arabidopsis*, proteins and lipids are the major reserves in mature seeds (Mansfield and Briarty, Can. J. Bot. 70:151, 1992; FIGS. 1A and 1B). To study the deposition of these reserves, a shrunken seed 1 (sse1) mutant that alters this seed storage profile by accumulating starch over proteins and lipids was isolated (FIGS. 1C and 1D). The cotyledon and the hypocotyl cells of sse1 contained no recognizable protein bodies and few oil bodies. Starch granules, membrane stacks, vesicles, and vacuoles, all of which were absent in wild type cells, were present in sse1 cells, and the oil bodies in sse1 contained higher electron density substances than the wild type. Additionally, the sse1 seeds were observed to shrink upon desiccation (a likely consequence of insufficient deposition of storage molecules), whereas the wild type seeds were desiccation tolerant (FIGS. 1E and 1F).

The sse1 mutant was identified in a transferred DNA (T-DNA) transgenic line (T line) that exhibited the shrunken seed phenotype as follows. The cDNA of the *Arabidopsis* prohibitin gene Atphb1 (Genbank Accession Number: U66591) in an antisense orientation was inserted into pBI121 (Clontech, LaJolla, Calif.) between the SacI and BamHI sites to replaced the β-glucuronidase coding region. This construct was then used to transform *Arabidopsis thaliana* C24 according to standard methods. Approximately 2% of the C24 transgenic lines, resulting from transformation experiments, showed the shrunken seed phenotype (sse1). In addition, Northern blot analysis with an Atphb1 cDNA bottom strand probe showed that the Atphb1 mRNA level in sse1 was similar to that of the wild type.

Furthermore, among the T2 seeds on the T1 plant (the primary transgenic plant), 90% of the seeds were shrunken and 10% were normally rounded. The shrunken seeds were not viable, and plants grown from the round seeds produced ~90% shrunken seeds. Propagation of the transgenic line by self-pollination for 4 generation (to T5) showed that this pattern of inheritance continued for generations. However, after backcrossing the T2 line to wild-type plants, sse1 was observed to behave as a typical single recessive Mendelian gene. This was shown by reciprocally crossing T2 plants derived from round seeds to wild-type C24 plants. All $F_1$ seeds resulting from these crosses were round. The numbers of shrunken/round $F_2$ seeds in six single siliques were 11/39, 15/36, 12/39, 10/42, 11/36, and 10/40; these numbers were consistent with an expected segregation ratio of 1:3 ($\chi^2$=0.64, P>0.1).

Moreover, when the segregation patterns of $F_3$ families were observed, sse1 cosegregated with the T-DNA. In these experiments, two hundred and sixty $F_3$ seed families were obtained from individual F2 round seeds, and one hundred and eighty families segregated for both the shrunken and kanamycin resistant (conferred by the T-DNA) phenotypes, whereas the other 80 showed neither phenotype.

Cloning of a cDNA Encoding the SSE1 Gene

The SSE1 gene and its cDNA were cloned as follows. A 136-bp genomic DNA fragment flanking the T-DNA was isolated by the thermal asymmetric interlaced-polymerase chain reaction according to the methods described by Liu et al. (*Plant J*. 8:457–463, 1995) and used as a probe for screening a genomic library. A 17-kb genomic fragment isolated from a λ-FIXII *Arabidopsis* C24 genomic library was then used as a probe to screen an *Arabidopsis* seedling cDNA library which was prepared according to the methods described by Minet et al. (Plant J. 2:417, 1992). Two SSE1 cDNA clones were subsequently identified, and DNA sequencing of these clones revealed that both have identical 5' ends and both included stop codons. The 3' polyadenylation site was determined by 3' rapid amplification of cDNA ends (RACE) polymerase chain reaction (PCR) according to standard methods. The SSE1 cDNA sequence (SEQ ID NO:1) and its predicted amino acid sequence (SEQ ID NO:2) are shown in FIGS. 2A and 2B, respectively. SSE1 was found to reside within the BAC clones F17K2 and F4118 (GenBank Accession Numbers: AC003680 and AC004665, respectively). The SSE1 protein predicted by the open reading frame was found to differ from the F17K2.22 hypothetical protein due to discrepancies between the predicted and the actual splicing sites.

Genotype Determination by Single-Seed Polymerase Chain Reaction

Figure 3A:
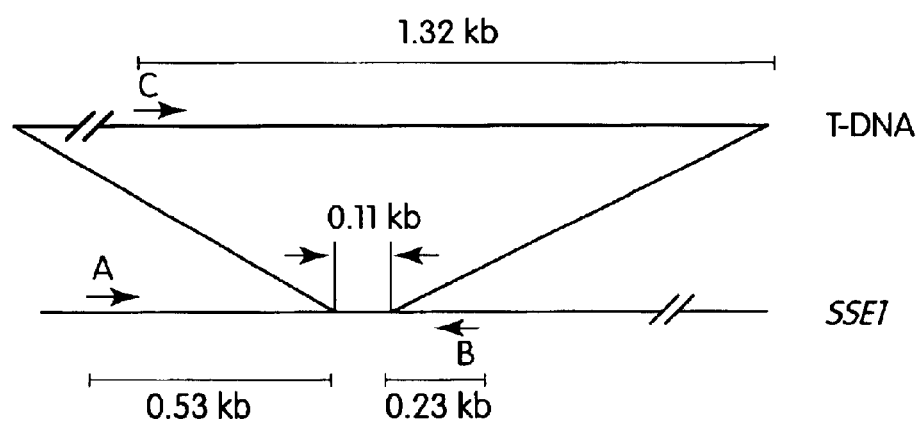
FIG. 3A is a PCR diagram showing that primers A and B amplify an ~0.9-kb fragment from the wild-type SSE1 allele, and primers C and B amplify an ~1.6-kb fragment from the T-DNA interrupted sse1 allele.

The SSE1 sequences obtained were then used to design three primers for determining the genotypes of shrunken and round seeds by single seed polymerase chain reaction (PCR) (FIG. 3A). These experiments were performed as follows. DNA was isolated from single embryos after removal of the seed coat, which had the same genotype as the parent. A single embryo was then transferred to an eppendorf tube containing 100 ml of grinding buffer, which consisted of 4 parts of homogenization buffer (100 mM NaCl, 200 mM sucrose, 100 mM EDTA, and 30 mM Tris-HCl; pH=8.0) and 1 part of phage lysis buffer (250 mM EDTA, 50 mM Tris-HCl, and 2.5% SDS; pH=9.2), and the embryo was ground with an eppendorf pestle. After incubation at 65° C. for 20 minutes, 33.3 ml of 3 M potassium acetate (pH 5.2) was added and the reaction was incubated on ice for 20 minutes. The mixture was centrifuged and the supernatant was mixed with 175 ml ethanol to precipitate the DNA. The DNA was dissolved in 20 ml of water and 1 ml of DNA was used in a 20 ml PCR reaction. As shown in FIG. 3A, primer A (5'-ATCAGAGATTGATTTAACGTA-3'; SEQ ID NO:3) and B (5'-ACGATTTTCAATTATGTGTTC-3'; SEQ ID NO:4) recognized SSE1 gene and amplified an ~0.9-kb fragment from the wild-type SSE1 allele. Primer C (5'-CGCTTGGTCGGTCATTTCG-3'; SEQ ID NO:5) recognized the neomycin phosphotransferase gene in the T-DNA. Primers B and C therefore amplified an ~1.6-kb fragment from the mutant sse1 allele. The PCR was performed with an annealing temperature of 56° C.

Figure 3B:
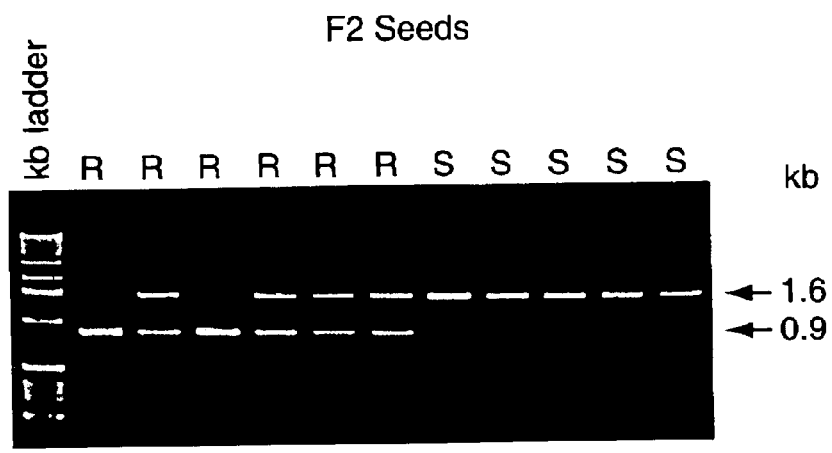
FIG. 3B shows the single seed PCR results of round (R) and shrunken (S) seeds in a $F_2$ population derived from a backcross between a T2 and a wild-type plant.
Figure 3C:
FIG. 3C shows the representative single seed PCR results of round (R) (n=13) and shrunken (S) (n=21) T4 seeds. A control reaction from a wild-type (WT) seed is also shown.

The results of the single-seed PCR experiments showed that 66% (n=6) of round $F_2$ seeds were heterozygous and 33% were homozygous for the wild-type allele, whereas 100% (n=5) of shrunken $F_2$ seeds were homozygous for the T-DNA insertion (FIG. 3B). T4 seeds were also analyzed. All round seeds (n=13) were heterozygous and all shrunken seeds (n=21) were homozygous for the T-DNA insertion (FIG. 3C). Thus, sse1 is recessive, and in the self-pollinated T line the mutant allele is transmitted at a higher frequency than the wild-type allele. For this analysis, $F_1$ seeds were obtained from reciprocal crosses between a round seed-derived T3 plant and a wild-type plant. Their genotypes were then examined to determine the genotypes of the gametes from the T3 plant. The wild-type allele was present in 3 out of 39 eggs and 0 out of 51 sperms; the rest of the gametes carried the mutant allele. Therefore, the T4 progeny would be either homozygous sse1 ($36/39=92\%$) or heterozygous ($3/39=8\%$).

Amino Acid Sequence Analysis and SSE1 Complementation of the Arabidopsis sse1 and Y. lipolytica pex16 Mutants The SSE1 cDNA encodes a predicted protein of 367 amino acids (SEQ ID NO:2; FIGS. 2B and 4A). Expression of SSE1 cDNA in transgenic sse1 plants was found to complement the shrunken seed phenotype (FIG. 4B). sse1 plants were complemented with SSE1 as follows. The SSE1 cDNA was fused with the 35S promoter (35SP) and the nopaline synthase 3' region (NOS 3'). The 35SP-SSE1-NOS3' cassette was subcloned into the KpnI site of the pLVN19R binary vector to make the pLVN19R-SSE1 construct. T3 plants from round seeds were then vacuum infiltrated with Agrobacterium tumefaciens strain GV3101 (Bechtold et al., C. R. Acad. Sci. Paris Life Sci. 316:1194, 1993) carrying pLVN19R-SSE1. Genotypes of seven methotrexate resistant transgenic plants were determined by PCR and six were found to be homozygous sse1. Four transgenic sse1 plants were fertile and produced complemented T2 seeds at 67 to 87%.

Similar to wild type, transgenic sse1 seeds expressing SSE1 were tolerant of desiccation, and cells were filled with storage proteins and lipids, but lacked starch. As shown in FIG. 4A, the SSE1 sequence showed similarity to Pex16p, a membrane associated protein required for the assembly and proliferation of peroxisomes (Eitzen et al., supra) and for the trafficking of plasma membrane and cell wall associated proteins (Titorenko et al., Mol. Cell. Biol. 17:5210, 1997), in the yeast Y. lipolytica. Pex16p is glycosylated and transiently localized in the endoplasmic reticulum (ER) (Titorenko and Rachubinski, supra). Despite the limited amino acid sequence similarity (26% identity), the two proteins have similar arrangements of their hydrophobic and hydrophilic regions (FIG. 4A). A predicted glycosylation site was found in SSE1 (FIG. 4A). SSE1 was also found to complement the growth of pex16 mutants on oleic acid as sole carbon source (FIG. 4C); indicating restoration of peroxisomal function (Eitzen et al., supra). The restoration of limited growth of the disruption allele P16KO-8A (Eitzen et al., supra) indicated that SSE1 cannot fully replace Pex16p in peroxisome formation, probably due to the functional difference(s) between the two proteins. In addition, SSE1 partially complemented the pex16-1 mutant for the dimorphic transition from yeast to the mycelia form (FIG. 4D). Pex16p is normally required for mycelia phase specific cell surface protein transport.

Peroxisomes are not generally found in dry seeds (Olsen and Harada, Annu. Rev. Plant Physiol. Plant Mol. Biol. 46:123, 1995 and references cited therein; FIG. 1). Protein and oil bodies are the most abundant organelles in mature Arabidopsis seeds and the formation of both is ER-dependent (Mansfield and Briarty, supra; Chrispeels, Annu. Rev. Plant Physiol. Plant Mol. Biol. 42, 21, 1991; Sarmiento et al., Plant J. 11:783, 1997; and Huang, Plant Physiol. 110:1055, 1996). By analogy to the function of Pex16p's in peroxisome assembly and cell surface protein transport, SSE1 could participate in oil body formation and storage protein delivery. The vesicles and stacks of membranes in the sse1 cells (FIG. 1D) resemble the subcellular structures in the pex16-1 mutant of Y. lipolytica (Eitzen et al., supra). The similarities between oil body and peroxisome biogenesis are consistent with their related functions in germinating seedlings of fat-metabolizing plants, where oil bodies are broken down by glyoxysomes (Olsen and Harada, supra).

Competitive RT-PCR Analyses of SSE1 Expression Profiles

SSE1 gene expression was also analyzed by competitive reverse transcription-polymerase chain reaction (RT-PCR): The amount of SSE1 mRNA obtained from different tissues and organs was determined as the target-to-competitor cDNA ratio as follows. After deoxyribonuclease treatment, 1 mg RNA was reverse transcribed in a 20 ml reaction, with 0.4 mM of the SSE1 specific primer FP15R (5'-GGCAATATTCTTCCGTTGC-3'; SEQ ID NO:7). Subsequently, 1 ml of the reverse transcription mixture and $5 \times 10^{-21}$ mol of competitor cDNA were used in each 20 ml PCR reaction. The competitor cDNA was identical to the SSE1 cDNA (designated target cDNA) except for a 95-bp internal deletion from the EcoRI to the NcoI site. The primers FP7 (5'-AAAAATGGAACTACATTATTCTC-3'; SEQ ID NO:8) and FP14R (5'-ATAAGTAAAACGCTTAACCTHC-3'; SEQ ID NO:9) amplify 814- and 719-bp fragments respectively, from the target and the competitor cDNAs. The ratio of the two PCR products reflected the relative amount of SSE1 cDNA (or mRNA) in each sample (Siebert and Larrick, Nature 359:557, 1992). The results of these experiments are depicted in FIG. 5.

SSE1 steady state mRNA level in the siliques increased during seed maturation to a maximum in mature 19- and 21-day-old brown siliques. The level of mRNA was also high in cotyledons of germinating seedlings and flowers, but low in expanding leaves and roots. Glyoxysomes are assembled in germinating seedlings (Olsen and Harada, supra); therefore SSE1 is likely to be required in this process. The low expression in expanding leaves, where leaf peroxisomes are formed, may be due to low peroxisomes abundance. Alternatively, SSE1 may not normally be involved in peroxisome/glyoxysome formation; rather its expression in germinating seedlings may be required for maintenance of the remaining oil bodies. The high expression levels in flowers suggests additional functions of SSE1, possibly the formation of oil body like organelles in tapetum and pollen (Huang, supra).

Efficient use of limited amounts of assimilates for seed storage deposition requires coordinated metabolic pathways and organelle assembly. In sse1 mature embryos, cotyledon and hypocotyl cells accumulated excess starch (FIG. 1). The functional similarity of SSE1 and Pex16p argues against SSE1 being a direct inhibitor of starch synthesis; rather, it implies that protein and oil body proliferation repress starch accumulation. Starch accumulation may also be a secondary effect of the lec mutations (Meinke et al., Plant Cell 6:1049, 1994). Consistent with the observations in *Arabidopsis*, simultaneous reduction in storage proteins and increase in starch content was also observed in a soybean shriveled seed mutant (Chen et al., Am. J. Bot. 85:492, 1998). Thus, in at least some species of flowering plants, starch accumulation maybe a default storage deposition pathway during seed development.

Isolation of Other SSE Genes

Any cell or tissue can serve as the nucleic acid source for the molecular cloning of an SSE gene. Isolation of an SSE gene involves the isolation of those DNA sequences which encode a protein exhibiting SSE-associated structures, properties, or activities, for example, the ability to complement an sse1 phenotype. Based on the SSE gene and polypeptide described herein, the isolation of additional plant SSE coding sequences (e.g., those sequences derived from monocots or dicots) is made possible using standard strategies and techniques that are well known in the art.

In one particular example, the SSE sequences described herein may be used, together with conventional screening methods of nucleic acid hybridization screening. Such hybridization techniques and screening procedures are well known to those skilled in the art and are described, for example, in Benton and Davis, Science 196:180, 1977; Grunstein and Hogness, Proc. Natl. Acad. Sci., USA 72:3961, 1975; Ausubel et al., *Current Protocols in Molecular Biology*, Wiley Interscience, New York; Berger and Kimmel, *Guide to Molecular Cloning Techniques*, 1987, Academic Press, New York; and Sambrook et al., *Molecular Cloning: A Laboratory Manual*, Cold Spring Harbor Laboratory Press, New York. In one particular example, all or part of the SSE1 cDNA (described herein) may be used as a probe to screen a recombinant plant DNA library for genes having sequence identity to the SSE gene. Hybridizing sequences are detected by plaque or colony hybridization according to the methods described below.

Alternatively, using all or a portion of the amino acid sequence of the SSE polypeptide, one may readily design SSE-specific oligonucleotide probes, including SSE degenerate oligonucleotide probes (i.e., a mixture of all possible coding sequences for a given amino acid sequence). These oligonucleotides may be based upon the sequence of either DNA strand and any appropriate portion of the SSE sequence (FIG. 2A; SEQ ID NO:1). General methods for designing and preparing such probes are provided, for example, in Ausubel et al., (supra), and Berger and Kimmel, (supra). These oligonucleotides are useful for SSE gene isolation, either through their use as probes capable of hybridizing to SSE complementary sequences or as primers for various amplification techniques, for example, polymerase chain reaction (PCR) cloning strategies. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

In one particular example of this approach, related SSE sequences having greater than 80% identity are detected or isolated using high stringency conditions. High stringency conditions may include hybridization at about 42° C. and about 50% formamide, 0.1 mg/mL sheared salmon sperm DNA, 1% SDS, 2× SSC, 10% Dextran sulfate, a first wash at about 65° C., about 2× SSC, and 1% SDS, followed by a second wash at about 65° C. and about 0.1× SSC. Alternatively, high stringency conditions may include hybridization at about 42° C. and about 50% formamide, 0.1 mg/mL sheared salmon sperm DNA, 0.5% SDS, 5× SSPE, 1× Denhardt's, followed by two washes at room temperature and 2× SSC, 0.1% SDS, and two washes at between 55–60° C. and 0.2× SSC, 0.1% SDS.

In another approach, low stringency hybridization conditions for detecting SSE genes having about 30% or greater sequence identity to the SSE genes described herein include, for example, hybridization at about 42° C. and 0.1 mg/mL sheared salmon sperm DNA, 1% SDS, 2× SSC, and 10% Dextran sulfate (in the absence of formamide), and a wash at about 37° C. and 6× SSC, about 1% SDS. Alternatively, the low stringency hybridization may be carried out at about 42° C. and 40% formamide, 0.1 mg/mL sheared salmon sperm DNA, 0.5% SDS, 5× SSPE, 1× Denhardt's, followed by two washes at room temperature and 2× SSC, 0.1% SDS and two washes at room temperature and 0.5× SSC, 0.1% SDS. These stringency conditions are exemplary; other appropriate conditions may be determined by those skilled in the art.

If desired, competitive RT-PCR or RNA gel blot analysis of total or poly(A+) RNAs isolated from any plant (e.g., those crop plants described herein) may be used to determine the presence or absence of an SSE transcript using conventional methods.

As discussed above, SSE oligonucleotides may also be used as primers in amplification cloning strategies, for example, using PCR. PCR methods are well known in the art and are described, for example, in *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, SSE sequences may be isolated using the PCR "RACE" technique, or Rapid Amplification of cDNA Ends (see, e.g., Innis et al. (supra)). By this method, oligonucleotide primers based on an SSE sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85:8998, 1988.

Alternatively, any plant cDNA or cDNA expression library may be screened by functional complementation of an sse mutant (for example, the sse1 mutant described herein) according to standard methods described herein.

Confirmation of a sequence's relatedness to the SSE polypeptide family may be accomplished by a variety of conventional methods including, but not limited to, functional complementation assays and sequence comparison of the gene and its expressed product. In addition, the activity of the gene product may be evaluated according to any of the techniques described herein, for example, the functional or immunological properties of its encoded product.

Once an SSE sequence is identified, it is cloned according to standard methods and used for the construction of plant expression vectors as described below.

SSE Polypeptide Expression

SSE polypeptides may be expressed and produced by transformation of a suitable host cell with all or part of an SSE cDNA (for example, the SSE cDNA (SEQ ID NO:1) described above) in a suitable expression vehicle or with a plasmid construct engineered for increasing the expression of an SSE polypeptide (supra) in vivo.

Those skilled in the field of molecular biology will understand that any of a wide variety of expression systems may be used to provide the recombinant protein. The precise host cell used is not critical to the invention. The SSE protein may be produced in a prokaryotic host, for example, *E. coli*, or in a eukaryotic host, for example, *Saccharomyces cerevisiae*, mammalian cells (for example, COS 1 or NIH 3T3 cells), or any of a number of plant cells or whole plant including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, conifers, petunia, tomato, potato, pepper, tobacco, *Arabidopsis*, grape, lettuce, sunflower, oilseed rape, flax, cotton, sugarbeet, celery, soybean, alfalfa, *Medicago*, lotus, *Vigna*, cucumber, carrot, eggplant, cauliflower, horseradish, morning glory, poplar, walnut, apple, grape, asparagus, cassava, rice, maize, millet, onion, barley, orchard grass, oat, rye, and wheat.

Such cells are available from a wide range of sources including the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I. K., *Cell Culture and Somatic Cell Genetics of Plants*, Vol I, II, III Laboratory Procedures and Their Applications Academic Press, New York, 1984; Dixon, R. A., *Plant Cell Culture-A Practical Approach*, IRL Press, Oxford University, 1985; Green et al., *Plant Tissue and Cell Culture*, Academic Press, New York, 1987; and Gasser and Fraley, Science 244:1293, 1989.

For prokaryotic expression, DNA encoding an SSE polypeptide is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors are found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., Nature 198:1056, 1977), the tryptophan (Trp) (Goeddel et al., Nucl. Acids Res. 8:4057, 1980), and the tac promoter systems, as well as the lambda-derived $P_L$ promoter and N-gene ribosome binding site (Simatake et al., Nature 292:128, 1981).

One particular bacterial expression system for SSE polypeptide production is the *E. coli* pET expression system (Novagen, Inc., Madison, Wis.). According to this expression system, DNA encoding an SSE polypeptide is inserted into a pET vector in an orientation designed to allow expression. Since the SSE gene is under the control of the T7 regulatory signals, expression of SSE is induced by inducing the expression of T7 RNA polymerase in the host cell. This is typically achieved using host strains which express T7 RNA polymerase in response to IPTG induction. Once produced, recombinant SSE polypeptide is then isolated according to standard methods known in the art, for example, those described herein.

Another bacterial expression system for SSE polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3x may be cleaved with factor Xa.

For eukaryotic expression, the method of transformation or transfection and the choice of vehicle for expression of the SSE polypeptide will depend on the host system selected. Transformation and transfection methods are described, e.g., in Ausubel et al. (supra); Weissbach and Weissbach, *Methods for Plant Molecular Biology*, Academic Press, 1989; Gelvin et al., *Plant Molecular Biology Manual*, Kluwer Academic Publishers, 1990; Kindle, K., Proc. Natl. Acad. Sci., U.S.A. 87:1228, 1990; Potrykus, I., Annu. Rev. Plant Physiol. Plant Mol. Biology 42:205, 1991; and BioRad (Hercules, Calif.) Technical Bulletin #1687 (Biolistic Particle Delivery Systems). Expression vehicles may be chosen from those provided, e.g., in *Cloning Vectors: A Laboratory Manual* (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above. Other expression constructs are described by Fraley et al. (U.S. Pat. No. 5,352,605).

Construction of Plant Transgenes

Most preferably, an SSE polypeptide is produced by a stably-transfected plant cell line, a transiently-transfected plant cell line, or by a transgenic plant. A number of vectors suitable for stable or extrachromosomal transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra).

Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once the desired SSE nucleic acid sequence is obtained as described above, it may be manipulated in a variety of ways known in the art. For example, where the sequence involves non-coding flanking regions, the flanking regions may be subjected to mutagenesis.

The SSE DNA sequence of the invention may, if desired, be combined with other DNA sequences in a variety of ways. The SSE DNA sequence of the invention may be employed with all or part of the gene sequences normally associated with the SSE protein. In its component parts, a DNA sequence encoding an SSE protein is combined in a DNA construct having a transcription initiation control region capable of promoting transcription and translation in a host cell.

In general, the constructs will involve regulatory regions functional in plants which provide for modified production of SSE protein as discussed herein. The open reading frame coding for the SSE protein or functional fragment thereof will be joined at its 5' end to a transcription initiation regulatory region such as the sequence naturally found in the 5' upstream region of the SSE structural gene. Numerous other transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well. Transcript termination regions may be provided by the DNA sequence encoding the SSE protein or any convenient transcription termination region derived from a different gene source. The transcript termination region will contain preferably at least 1–3 kb of sequence 3' to the structural gene from which the termination region is derived. Plant expression constructs having SSE as the DNA sequence of interest for expression (in either the sense or antisense orientation) may be employed with a wide variety of plant life, particularly plant life involved in the production of storage reserves (for example, those involving carbon and nitrogen metabolism). Such genetically-engineered plants are useful for a variety of industrial and agricultural applications as discussed infra. Importantly, this invention is applicable to dicotyledons and monocotyledons, and will be readily applicable to any new or improved transformation or regeneration method.

The expression constructs include at least one promoter operably linked to at least one SSE gene. An example of a useful plant promoter according to the invention is a *caulimovirus* promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. Examples of plant expression constructs using these promoters are found in Fraley et al., U.S. Pat. No. 5,352,605. In most tissues of transgenic plants, the CaMV 35S promoter is a strong promoter (see, e.g., Odell et al., Nature 313:810, 1985). The CaMV promoter is also highly active in monocots (see, e.g., Dekeyser et al., Plant Cell 2:591, 1990; Terada and Shimamoto, Mol. Gen. Genet. 220:389, 1990). Moreover, activity of this promoter can be further increased (i.e., between 2–10 fold) by duplication of the CaMV 35S promoter (see e.g., Kay et al., Science 236:1299, 1987; Ow et al., Proc. Natl. Acad. Sci., U.S.A. 84:4870, 1987; and Fang et al., Plant Cell 1:141, 1989, and McPherson and Kay, U.S. Pat. No. 5,378,142).

Other useful plant promoters include, without limitation, the nopaline synthase (NOS) promoter (An et al., Plant Physiol. 88:547, 1988 and Rodgers and Fraley, U.S. Pat. No. 5,034,322), the octopine synthase promoter (Fromm et al., Plant Cell 1:977, 1989), figwort mosiac virus (FMV) promoter (Rogers, U.S. Pat. No. 5,378,619), and the rice actin promoter (Wu and McElroy, WO91/09948).

Exemplary monocot promoters include, without limitation, commelina yellow mottle virus promoter, sugar cane badna virus promoter, rice tungro baciliform virus promoter, maize streak virus element, and wheat dwarf virus promoter.

For certain applications, it may be desirable to produce the SSE gene product in an appropriate tissue, at an appropriate level, or at an appropriate developmental time. For this purpose, there are an assortment of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression (see, e.g., Callis et al., Plant Physiol. 88:965, 1988; Takahashi and Komeda, Mol. Gen. Genet. 219:365, 1989; and Takahashi et al. Plant J. 2:751, 1992), light-regulated gene expression (e.g., the pea rbcS-3A described by Kuhlemeier et al., Plant Cell 1:471, 1989; the maize rbcS promoter described by Schäffner and Sheen, Plant Cell 3:997, 1991; the chlorophyll a/b-binding protein gene found in pea described by Simpson et al., EMBO J. 4:2723, 1985; the Arabssu promoter; or the rice rbs promoter), hormone-regulated gene expression (for example, the abscisic acid (ABA) responsive sequences from the Em gene of wheat described by Marcotte et al., Plant Cell 1:969, 1989; the ABA-inducible HVA1 and HVA22, and rd29A promoters described for barley and *Arabidopsis* by Straub et al., Plant Cell 6:617, 1994 and Shen et al., Plant Cell 7:295, 1995; and wound-induced gene expression (for example, of wunI described by Siebertz et al., Plant Cell 1:961, 1989), organ-specific gene expression (for example, of the tuber-specific storage protein gene described by Roshal et al., EMBO J. 6:1155, 1987; the 23-kDa zein gene from maize described by Schernthaner et al., EMBO J. 7:1249, 1988; or the French bean β-phaseolin gene described by Bustos et al., Plant Cell 1:839, 1989), or pathogen-inducible promoters (for example, PR-1, prp-1, or β-1,3 glucanase promoters, the fungal-inducible wirla promoter of wheat, and the nematode-inducible promoters, TobRB7-5A and Hmg-1, of tobacco and parsley, respectively).

Plant expression vectors may also optionally include RNA processing signals, e.g, introns, which have been shown to be important for efficient RNA synthesis and accumulation (Callis et al., Genes and Dev. 1:1183, 1987). The location of the RNA splice sequences can dramatically influence the level of transgene expression in plants. In view of this fact, an intron may be positioned upstream or downstream of an SSE polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl. Acad. Sci. U.S.A. 84:744, 1987; An et al., Plant Cell 1:115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 µg/mL (kanamycin), 20–50 µg/mL (hygromycin), or 5–10 µg/mL (bleomycin). A useful strategy for selection of transformants for herbicide resistance is described, e.g., by Vasil et al., supra.

In addition, if desired, the plant expression construct may contain a modified or fully-synthetic structural SSE coding sequence which has been changed to enhance the performance of the gene in plants. Methods for constructing such a modified or synthetic gene are described in Fischoff and Perlak, U.S. Pat. No. 5,500,365.

It will also be readily appreciated by those skilled in the art that a wide variety of methods are known for engineering transgene constructs which silence or inactivate an endogenous gene. Homologous recombination is but one of the methods known to those skilled in the art for rendering an endogenous gene inoperative. Thus, when the engineered gene is homologously recombined into the plant, the endogenous gene will be rendered inoperative. An overview of this general process is provided in Yoder et al. ("Progress Towards Gene Targeting in Plants," Genetic Engineering, Vol. 13, Plenum Press, New York, 1991). Accordingly, gene targeting can be used to silence or replace the endogenous gene with an engineered allele; thus the phenotype of the altered gene, or its regulatory sequences, can be evaluated in planta. In addition, methods for constructing transgene constructs for silencing or inactivating gene expression in plants using antisense or co-suppression technologies are well known in the art.

It should be readily apparent to one skilled in the art of molecular biology, especially in the field of plant molecular biology, that the level of gene expression of a transgene construct is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) *Agrobacterium*-mediated transformation (*A. tumefaciens* or *A. rhizogenes*) (see, e.g., Lichtenstein and Fuller In: *Genetic Engineering*, vol 6, P W J Rigby, ed, London, Academic Press, 1987; and Lichtenstein, C. P., and Draper, J, In: *DNA Cloning*, Vol II, D. M. Glover, ed, Oxford, IRI Press, 1985)), (2) the particle delivery system (see, e.g., Gordon-Kamm et al., Plant Cell 2:603 (1990); or BioRad Technical Bulletin 1687, supra), (3) microinjection protocols (see, e.g., Green et al., supra), (4) polyethylene glycol (PEG) procedures (see, e.g., Draper et al., Plant Cell Physiol. 23:451, 1982; or e.g., Zhang and Wu, Theor. Appl. Genet. 76:835, 1988), (5) liposome-mediated DNA uptake (see, e.g., Freeman et al., Plant Cell Physiol. 25:1353, 1984), (6) electroporation protocols (see, e.g., Gelvin et al., supra; Dekeyser et al., supra; Fromm et al., Nature 319:791, 1986; Sheen Plant Cell 2:1027, 1990; or Jang and Sheen Plant Cell 6:1665, 1994), and (7) the vortexing method (see, e.g., Kindle supra). The method of transformation is not critical to the invention. Any method which provides for efficient transformation may be employed. As newer methods are available to transform crops or other host cells, they may be directly applied. Suitable plants for use in the practice of the invention include, but are not limited to, sugar cane, wheat, rice, maize, sugar beet, potato, barley, manioc, sweet potato, soybean, sorghum, cassava, banana, grape, oats, tomato, millet, coconut, orange, rye, cabbage, apple, watermelon, canola, cotton, carrot, garlic, onion, pepper, strawberry, yam, peanut, onion, bean, pea, mango, citrus plants, walnuts, and sunflower.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned SSE polypeptide construct under the control of the 35S CaMV promoter and the nopaline synthase terminator and carrying a selectable marker (for example, kanamycin resistance) is transformed into *Agrobacterium*. Transformation of leaf discs (for example, of tobacco or potato leaf discs), with vector-containing *Agrobacterium* is carried out as described by Horsch et al. (*Science* 227:1229, 1985). Putative transformants are selected after a few weeks (for example, 3 to 5 weeks) on plant tissue culture media containing kanamycin (e.g. 100 μg/mL). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using SSE specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

In addition, if desired, once the recombinant SSE protein is expressed in any cell or in a transgenic plant (for example, as described above), it may be isolated, e.g., using affinity chromatography. In one example, an anti-SSE polypeptide antibody (e.g., produced as described in Ausubel et al., supra, or by any standard technique) may be attached to a column and used to isolate the polypeptide. Lysis and fractionation of SSE-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, *Laboratory Techniques In Biochemistry And Molecular Biology*, eds., Work and Burdon, Elsevier, 1980).

Polypeptides of the invention, particularly short SSE protein fragments, can also be produced by chemical synthesis (e.g., by the methods described in *Solid Phase Peptide Synthesis*, 2nd ed., 1984 The Pierce Chemical Co., Rockford, Ill.). These general techniques of polypeptide expression and purification can also be used to produce and isolate useful SSE fragments or analogs.

Engineering Storage Reserve Materials

As discussed above, plasmid constructs designed for the expression of SSE gene products are useful, for example, for modifying or altering seed or vegetative storage reserve profiles. SSE genes that are isolated from a host plant (e.g., *Arabidopsis* or *Brassica*) may be engineered for increased or decreased expression in the same plant, a closely related species, or a distantly related plant species. For example, the cruciferous *Arabidopsis* SSE1 gene may be engineered for constitutive expression and then transformed into an *Arabidopsis* host plant. Alternatively, the *Arabidopsis* SSE1 gene may be engineered for expression other cruciferous plants, such as the *Brassicas* (for example, broccoli, cabbage, and cauliflower). Evaluation of the modification conferred on a plant by ectopic expression of an SSE gene is determined according to conventional methods and assays (for example, those described herein).

In one working example, constitutive expression of the SSE1 gene of *Arabidopsis* (FIG. 2A; SEQ ID NO:1) is used to alter seed storage reserve deposition in transgenic seeds of *Brassica*. In one particular example, a plant expression vector is constructed that contains an SSE1 cDNA sequence expressed under the control of the enhanced CaMV 35S promoter as described by McPherson and Kay (U.S. Pat. No. 5,359,142). This expression vector is then used to transform *Brassica* according to the methods described in Moloney et al. (U.S. Pat. No. 5,750,827). Seeds of transformed *Brassica* and control plants are then profiled for storage reserve material according to conventional methods to determine the qualitative and quantitative aspects of the deposited reserve materials. Transformed plants that express an SSE1 gene and produce seeds having an increased level of storage reserve material (e.g., reserve lipid or storage protein) relative to control plants are taken as being useful in the invention.

In another working example, gene silencing or inactivation technologies may also be used to modify or alter the deposition of seed storage reserve material. Exemplary methods for silencing or inactivating plant gene expression include antisense RNA (Shewmaker et al., U.S. Pat. No. 5,107,065), co-suppression (Napoli et al, U.S. Pat. No. 5,034,327), and homologous recombination (Offringa et al., U.S. Pat. No. 5,501,967). For example, a plant expression vector is constructed that contains an antisense SSE1 which is expressed under the control of the enhanced CaMV 35S promoter as described by McPherson and Kay, supra and Shewmaker at al. (U.S. Pat. No. 5,107,065). This expression vector is then used to transform *Brassica* according to the methods described in Moloney et al., supra. To assess reserve material deposition, transformed plants and appropriate controls are grown, and the storage reserves of their seeds are evaluated according to standard methods, for example, those described herein. Transformed *Brassica* plants that express an antisense SSE1 sequence and that produce seeds having a decreased level of reserve material relative to control plants are taken as being useful in the invention.

Engineering Stress-Protected Plants

As discussed above, because constitutive expression of an SSE1 has been found to confer dessication tolerance, constructs designed for the expression of an SSE polypeptide (or an SSE1 homolog) are useful for generating transgenic seeds having an increased level of tolerance to environmental stress. To achieve such tolerance, it is important to express such a protein at an effective level in a transgenic seed. Seed-specific gene promoters are especially useful for this purpose. Evaluation of the level of stress protection conferred to a seed by expression of a DNA sequence expressing an SSE1 polypeptide is determined according to conventional methods and assays as described below.

In one working example, seed-specific expression of an SSE gene, for example, the SSE1, is used in *Brassica* to enhance salt stress tolerance. For example, a plant expression vector is constructed that contains an SSE1 sequence expressed under the control of a *Brassica* seed-specific promoter. This expression vector is then used to transform *Brassica* according to standard methods. To assess salt tolerance, seeds obtained from transformed *Brassica* plants and appropriate controls are evaluated according to standard methods. Transgenic seeds containing the gene are germinated in the presence of various salt or osmotically active solutions to determine whether transgenic seeds demonstrate increased tolerance or resistance to salt stress. If desired, seedlings can also be grown in hydroponic systems and challenged with salt or agents of differing osmotic potentials at different, or all, developmental stages in order to assess the response of SSE1-expressing plants to these stresses. Growth and physiological measurements are used to document the differences. Transformed *Brassica* plants which produce seeds having an increased level of salt tolerance relative to control plants are taken as being useful in the invention.

Engineering Plants Having Increased Yield/Productivity

Seeds of transgenic plants expressing a recombinant SSE gene (or an SSE1 homolog) are planted out in test plots, and their agronomic performance is compared to standard plants using techniques familiar to those of skill in the art. Optionally included in this comparison are plants of similar genetic background without the transgene. A yield benefit is observed and plants exhibiting the increased yield are advanced for commercialization.

In addition, transgenic plants expressing an SSE gene (or an SSE1 homolog) are field tested for agronomic performance under conditions, including, but not limited to, limited or inadequate water availability. When compared to nontransgenic plants, transgenic plants expressing the SSE1 gene exhibit higher yield than their non-transgenic counterparts under non-optimal growing conditions.

SSE Interacting Polypeptides

The isolation of SSE sequences also facilitates the identification of polypeptides which interact with the SSE protein. Such polypeptide-encoding sequences are isolated by any standard two hybrid system (see, for example, Fields et al., Nature 340:245–246, 1989; Yang et al., Science 257:680–682, 1992; Zervos et al., Cell 72:223–232, 1993). For example, all or a part of the SSE sequence may be fused to a DNA binding domain (such as the GAL4 or LexA DNA binding domain). After establishing that this fusion protein does not itself activate expression of a reporter gene (for example, a lacZ or LEU2 reporter gene) bearing appropriate DNA binding sites, this fusion protein is used as an interaction target. Candidate interacting proteins fused to an activation domain (for example, an acidic activation domain) are then co-expressed with the SSE fusion in host cells, and interacting proteins are identified by their ability to contact the SSE sequence and stimulate reporter gene expression. SSE-interacting proteins identified using this screening method provide good candidates for proteins that are involved in the acquired resistance signal transduction pathway.

Antibodies

SSE polypeptides described herein (or imunogenic fragments or analogs) may be used to raise antibodies useful in the invention; such polypeptides may be produced by recombinant or peptide synthetic techniques (see, e.g., *Solid Phase Peptide Synthesis*, 2nd ed., 1984, Pierce Chemical Co., Rockford, Ill.; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the SSE polypeptides described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific SSE recognition by Western blot or immunoprecipitation analysis (by the methods described in Ausubel et al., supra). Antibodies which specifically recognize SSE polypeptides are considered to be useful in the invention; such antibodies may be used, e.g., in an immunoassay to monitor the level of SSE polypeptide produced by a plant.

Other Embodiments

The invention further includes analogs of any naturally-occurring plant SSE polypeptide. Analogs can differ from the naturally-occurring SSE protein by amino acid sequence differences, by post-translational modifications, or by both. Analogs of the invention will generally exhibit at least 40%, more preferably 50%, and most preferably 60% or even having 70%, 80%, or 90% identity with all or part of a naturally-occurring plant SSE amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring SSE polypeptide by alterations in primary sequence. These include genetic variants, both natural and induced (for example, resulting from random mutagenesis by irradiation or exposure to ethyl methylsulfate or by site-specific mutagenesis as described in Sambrook, Fritsch and Maniatis, supra, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes SSE polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of SSE polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). In preferred embodiments, an SSE polypeptide fragment includes an ankyrin-repeat motif as described herein. In other preferred embodiments, an SSE fragment is capable of interacting with a second polypeptide component of the SSE signal transduction cascade.

Furthermore, the invention includes nucleotide sequences that facilitate specific detection of an SSE nucleic acid. Thus, SSE sequences described herein or portions thereof may be used as probes to hybridize to nucleotide sequences from other plants (e.g., dicots, monocots, gymnosperms, and algae) by standard hybridization techniques under conventional conditions. Sequences that hybridize to an SSE coding sequence or its complement and that encode an SSE polypeptide are considered useful in the invention. As used herein, the term "fragment," as applied to nucleic acid sequences, means at least 5 contiguous nucleotides, preferably at least 10 contiguous nucleotides, more preferably at least 20 to 30 contiguous nucleotides, and most preferably at least 40 to 80 or more contiguous nucleotides. Fragments of SSE nucleic acid sequences can be generated by methods known to those skilled in the art.

All publications and patent applications mentioned in this specification are herein incorporated by reference to the same extent as if each independent publication or patent application was specifically and individually indicated to be incorporated by reference.

What is claimed is:

1. An isolated nucleic acid molecule encoding a polypeptide having at least 95% identity with SEQ ID NO:2, wherein silencing of expression of said nucleic acid molecule, in a plant, results in said plant having abnormal storage deposition and the shrunken phenotype of sse1 seeds.

2. The isolated nucleic acid molecule of claim 1, wherein the nucleic acid molecule comprises SEQ ID NO:1.

3. The isolated nucleic acid molecule of claim 1, wherein the polypeptide comprises SEQ ID NO:2.

4. A construct comprising a promoter operably linked to the isolated nucleic acid molecule of claim 1.

5. The construct of claim 4, wherein the promoter is a constitutive promoter.

6. The construct of claim 4, wherein the nucleic acid molecule is linked to the promoter in an antisense orientation.

7. An expression vector comprising a promoter operably linked to the isolated nucleic acid molecule of claim 1.

8. The expression vector of claim 7, wherein the nucleic acid molecule comprises SEQ ID NO:1.

9. The expression vector of claim 7, wherein the polypeptide comprises SEQ ID NO:2.

10. The expression vector of claim 7, wherein the promoter is an inducible promoter.

11. The expression vector of claim 7, wherein the promoter is a constitutive promoter.

12. The expression vector of claim 7, wherein the nucleic acid molecule is linked to the promoter in the antisense orientation.

13. A cell comprising the isolated nucleic acid molecule of claim 1.

14. The cell of claim 13, wherein the nucleic acid molecule comprises SEQ ID NO:1.

15. The cell of claim 13, wherein the polypeptide comprises SEQ ID NO:2.

16. The cell of claim 13, wherein said cell is a plant cell.

17. The cell of claim 13, wherein said cell is a bacterial cell.

18. A cell comprising the construct of claim 4.

19. The cell of claim 18, wherein the promoter is a constitutive promoter.

20. The cell of claim 18, wherein the isolated nucleic acid molecule is linked to the promoter in an antisense orientation.

21. A plant or plant component comprising the isolated nucleic acid molecule of claim 1.

22. The plant or plant component of claim 21, wherein the nucleic acid molecule comprises SEQ ID NO:1.

23. The plant or plant component of claim 21, wherein the polypeptide comprises SEQ ID NO:2.

24. The plant or plant component of claim 21, wherein said plant or plant component is an angiosperm.

25. The plant or plant component of claim 21, wherein said plant or plant component is a dicot.

26. The plant or plant component of claim 21, wherein said plant or plant component is a cruciferous plant.

27. The plant or plant component of claim 21, wherein said plant or plant component is a monocot.

28. A plant or plant component comprising the construct of claim 4.

29. The plant or plant component of claim 28, wherein the promoter is a constitutive promoter.

30. The plant or plant component of claim 28, wherein the nucleic acid molecule is linked to the promoter in the antisense orientation.

31. A seed comprising the isolated nucleic acid molecule of claim 1.

32. A cell from a plant or plant component of claim 21, wherein the cell comprises the nucleic acid molecule.

33. A plant regenerated from a cell of the plant or plant component of claim 21.

* * * * *

SEQUENCE LISTING

```
<160> NUMBER OF SEQ ID NOS:  9

<210> SEQ ID NO 1
<211> LENGTH: 1483
<212> TYPE: DNA
<213> ORGANISM: Arabidopsis thaliana

<400> SEQUENCE: 1
attgcaacca ggaagagaaa gaaaatcaga gattgattta acgtgaatgg aattttgttg      60
tttcccaaat tcttctgaga aatagcaaag ttcagttttg tttctctcta tctgaagctc     120
aatggaagct tataagcaat gggtttggag aaatagagag tatgtacaat cctttggatc     180
ctttgccaac ggattgacat ggctgcttcc tgagaagttt tctgcttcag agattggacc     240
agaagcagta acggctttt tgggcatatt cacaacgata aatgaacaca taattgaaaa      300
tgctccaaca cctcgtggcc atgttggatc ttccgggaat gatccatccc tttcttatcc     360
actactcatc gccatcctca aggatttgga aactgttgtg gaagtggcag ctgaacactt     420
ctatggagac aaaaaatgga actacattat tctcactgaa gctatgaagg ctgtcattag     480
gttagccttg ttccggaata gtgggtataa gatgcttctt caaggagggg aaacacctaa     540
tgaggagaaa gattctaacc aatccgagtc gcaaaataga gctggtaatt cgggtagaaa     600
```

-continued

```
tctcgggcct catggtcttg gaaaccaaaa tcatcataat ccatggaact tggaaggacg       660
ggcgatgtct gctttaagtt catttggtca gaatgcaaga acaacaacat cttctacccc       720
cggttggtct cgaagaattc aacatcagca agcagttata gagcctccaa tgatcaagga       780
gaggcgaaga acgatgtccg agctacttac tgagaagggt gttaatggag cgttgtttgc       840
gattggtgag gttctttaca taacgagacc gctcatttac gttcttttca tcagaaaata       900
tggagtccga tcttggattc cttgggctat atcgctttct gtggacacac tggggatggg       960
tcttcttgca aattcgaagt ggtggggaga aagagcaag caagtccatt tctcaggacc      1020
tgaaaaggat gagctgagga gacgaaaact gatatgggca ttgtacctca tgagagatcc      1080
attcttcacc aagtacacaa ggcagaagct ggaaagctct caaagaagc tggaactaat      1140
tccattgatc ggattcctca cagagaagat tgtggagctt ttggagggag ctcagtcacg      1200
gtacacttac atatcgggat cgtgaggtta agcgttttac ttatggttta tatgcaacgg      1260
aagaatattg ccattgttgg aatgcttttt tagatcatca aaggctccta cagatttctt      1320
agggaatggt ttcaggcttt tgttagaaat tgtgtttatt gcaacaggta gagaacataa      1380
ccatagacag atgtatctga agagataagc ttctctatgt ctaaagaaat ggaccgatac      1440
gaataaaaca agcatcatta aagattaaaa aaaaaaaaaa aaa                       1483
```

<210> SEQ ID NO 2
<211> LENGTH: 367
<212> TYPE: PRT
<213> ORGANISM: Arabidopsis thaliana

<400> SEQUENCE: 2

```
Met Glu Ala Tyr Lys Gln Trp Val Trp Arg Asn Arg Glu Tyr Val Gln
  1               5                  10                  15

Ser Phe Gly Ser Phe Ala Asn Gly Leu Thr Trp Leu Leu Pro Glu Lys
             20                  25                  30

Phe Ser Ala Ser Glu Ile Gly Pro Glu Ala Val Thr Ala Phe Leu Gly
         35                  40                  45

Ile Phe Thr Thr Ile Asn Glu His Ile Ile Glu Asn Ala Pro Thr Pro
     50                  55                  60

Arg Gly His Val Gly Ser Ser Gly Asn Asp Pro Ser Leu Ser Tyr Pro
 65                  70                  75                  80

Leu Leu Ile Ala Ile Leu Lys Asp Leu Glu Thr Val Val Glu Val Ala
                 85                  90                  95

Ala Glu His Phe Tyr Gly Asp Lys Lys Trp Asn Tyr Ile Ile Leu Thr
            100                 105                 110

Glu Ala Met Lys Ala Val Ile Arg Leu Ala Leu Phe Arg Asn Ser Gly
        115                 120                 125

Tyr Lys Met Leu Leu Gln Gly Gly Glu Thr Pro Asn Glu Glu Lys Asp
    130                 135                 140

Ser Asn Gln Ser Glu Ser Gln Asn Arg Ala Gly Asn Ser Gly Arg Asn
145                 150                 155                 160

Leu Gly Pro His Gly Leu Gly Asn Gln Asn His His Asn Pro Trp Asn
                165                 170                 175

Leu Glu Gly Arg Ala Met Ser Ala Leu Ser Ser Phe Gly Gln Asn Ala
            180                 185                 190

Arg Thr Thr Thr Ser Ser Thr Pro Gly Trp Ser Arg Arg Ile Gln His
        195                 200                 205

Gln Gln Ala Val Ile Glu Pro Pro Met Ile Lys Glu Arg Arg Arg Thr
    210                 215                 220
```

Met Ser Glu Leu Leu Thr Glu Lys Gly Val Asn Gly Ala Leu Phe Ala
225                 230                 235                 240

Ile Gly Glu Val Leu Tyr Ile Thr Arg Pro Leu Ile Tyr Val Leu Phe
                245                 250                 255

Ile Arg Lys Tyr Gly Val Arg Ser Trp Ile Pro Trp Ala Ile Ser Leu
            260                 265                 270

Ser Val Asp Thr Leu Gly Met Gly Leu Leu Ala Asn Ser Lys Trp Trp
            275                 280                 285

Gly Glu Lys Ser Lys Gln Val His Phe Ser Gly Pro Glu Lys Asp Glu
        290                 295                 300

Leu Arg Arg Arg Lys Leu Ile Trp Ala Leu Tyr Leu Met Arg Asp Pro
305                 310                 315                 320

Phe Phe Thr Lys Tyr Thr Arg Gln Lys Leu Glu Ser Ser Gln Lys Lys
                325                 330                 335

Leu Glu Leu Ile Pro Leu Ile Gly Phe Leu Thr Glu Lys Ile Val Glu
            340                 345                 350

Leu Leu Glu Gly Ala Gln Ser Arg Tyr Thr Tyr Ile Ser Gly Ser
        355                 360                 365

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
atcagagatt gatttaacgt a                                              21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
acgattttca attatgtgtt c                                              21

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
cgcttggtcg gtcatttcg                                                 19

<210> SEQ ID NO 6
<211> LENGTH: 391
<212> TYPE: PRT
<213> ORGANISM: Yarrowia lipolytica

<400> SEQUENCE: 6

Met Thr Asp Lys Leu Val Lys Val Met Gln Lys Lys Ser Ala Pro
1               5                   10                  15

Gln Thr Trp Leu Asp Ser Tyr Asp Lys Phe Leu Val Arg Asn Ala Ala
            20                  25                  30

Ser Ile Gly Ser Ile Glu Ser Thr Leu Arg Thr Val Ser Tyr Val Leu

```
                35                  40                  45
Pro Gly Arg Phe Asn Asp Val Glu Ile Ala Thr Glu Thr Leu Tyr Ala
    50                  55                  60

Val Leu Asn Val Leu Gly Leu Tyr His Asp Thr Ile Ile Ala Arg Ala
 65                  70                  75                  80

Val Ala Ala Ser Pro Asn Ala Ala Val Tyr Arg Pro Ser Pro His
                 85                  90                  95

Asn Arg Tyr Thr Asp Trp Phe Ile Lys Asn Arg Lys Gly Tyr Lys Tyr
                100                 105                 110

Ala Ser Arg Ala Val Thr Phe Val Lys Phe Gly Glu Leu Val Ala Glu
            115                 120                 125

Met Val Ala Lys Lys Asn Gly Gly Glu Met Ala Arg Trp Lys Cys Ile
        130                 135                 140

Ile Gly Ile Glu Gly Ile Lys Ala Gly Leu Arg Ile Tyr Met Leu Gly
145                 150                 155                 160

Ser Thr Leu Tyr Gln Pro Leu Cys Thr Thr Pro Tyr Pro Asp Arg Glu
                165                 170                 175

Val Thr Gly Glu Leu Leu Glu Thr Ile Cys Arg Asp Glu Gly Glu Leu
            180                 185                 190

Asp Ile Glu Lys Gly Leu Met Asp Pro Gln Trp Lys Met Pro Arg Thr
        195                 200                 205

Gly Arg Thr Ile Pro Glu Ile Ala Pro Thr Asn Val Glu Gly Tyr Leu
    210                 215                 220

Leu Thr Lys Val Leu Arg Ser Glu Asp Val Asp Arg Pro Tyr Asn Leu
225                 230                 235                 240

Leu Ser Arg Leu Asp Asn Trp Gly Val Val Ala Glu Leu Leu Ser Ile
                245                 250                 255

Leu Arg Pro Leu Ile Tyr Ala Cys Leu Leu Phe Arg Gln His Val Asn
            260                 265                 270

Lys Thr Val Pro Ala Ser Thr Lys Ser Lys Phe Pro Phe Leu Asn Ser
        275                 280                 285

Pro Trp Ala Pro Trp Ile Ile Gly Leu Val Ile Glu Ala Leu Ser Arg
    290                 295                 300

Lys Met Met Gly Ser Trp Leu Leu Arg Gln Arg Gln Ser Gly Lys Thr
305                 310                 315                 320

Pro Thr Ala Leu Asp Gln Met Glu Val Lys Gly Arg Thr Asn Leu Leu
                325                 330                 335

Gly Trp Trp Leu Phe Arg Gly Glu Phe Tyr Gln Ala Tyr Thr Arg Pro
            340                 345                 350

Leu Leu Tyr Ser Ile Val Ala Arg Leu Glu Lys Ile Pro Gly Leu Gly
        355                 360                 365

Leu Phe Gly Ala Leu Ile Ser Asp Tyr Leu Tyr Leu Phe Asp Arg Tyr
    370                 375                 380

Tyr Phe Thr Ala Ser Thr Leu
385                 390

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
ggcaatattc ttccgttgc                                                19
```

```
<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
aaaaatggaa ctacattatt ctc                                              23

<210> SEQ ID NO 9
<211> LENGTH: 22
<212> TYPE: DNA
<213> ORGANISM: Artificial Sequence
<220> FEATURE:
<223> OTHER INFORMATION: Primer
<221> NAME/KEY: variation
<222> LOCATION: (1)...(22)
<223> OTHER INFORMATION: Where h is a, c, or t/u; not g.

<400> SEQUENCE: 9
ataagtaaaa cgcttaacct hc                                               22
```